United States Patent
Tilley

(12) 
(10) Patent No.: US 6,284,296 B1
(45) Date of Patent: Sep. 4, 2001

(54) METHOD OF DOUGH MANUFACTURE BY MONITORING AND OPTIMIZING GLUTEN PROTEIN LINKAGES

(75) Inventor: Katherine Tilley, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/238,376

(22) Filed: Jan. 27, 1999

(51) Int. Cl.$^7$ .............................. G01N 33/10; A21D 2/00
(52) U.S. Cl. .................. 426/231; 426/504; 426/496; 426/549; 426/391; 426/23; 426/271
(58) Field of Search ...................... 426/231, 271, 426/391, 496, 504, 23, 233, 549

(56) References Cited

U.S. PATENT DOCUMENTS

| | | | | |
|---|---|---|---|---|
| 4,135,816 | * | 1/1979 | Niemann et al. .................... | 356/317 |
| 4,262,024 | * | 4/1981 | Mathason ............................ | 426/231 |
| 5,510,129 | * | 4/1996 | Kim ..................................... | 426/62 |
| 5,650,558 | | 7/1997 | Blechl et al. ....................... | 800/205 |

FOREIGN PATENT DOCUMENTS

| | | | | |
|---|---|---|---|---|
| 9808607 | 3/1998 | (WO) | ............................. | B02B/3/14 |
| 9848271 | 10/1998 | (WO) | ............................. | G01N/33/10 |
| 9903985 | 1/1999 | (WO) | ............................. | C12N/15/00 |

OTHER PUBLICATIONS

Michon, et al., "Wheat Prolamine Crosslinking Through Dityrosine Formation Catalyzed by Peroxidases: Improvement in the Modification of a Poorly Accessible Substrate by 'indirect' Catalysis," *Biotechnology and Bioengineering,* May 20, 1999, vol. 63, No. 4, p. 449–458.

Michon, et al., "Horseradish Peroxidase Oxidation of Tyrosine–Containing Peptides and Their Subsequent Polymerization: A Kinetic Study," *Biochemistry,* Nov. 28, 1997, vol. 36, p. 8504–8513.

* cited by examiner

*Primary Examiner*—Milton I. Cano
*Assistant Examiner*—Robert Madsen
(74) *Attorney, Agent, or Firm*—Hovey, Williams, Timmons & Collins

(57) ABSTRACT

Improved dough-forming processes (and resultant doughs) are provided by measuring the tyrosine content of starting wheat flour and/or analyzing doughs during manufacture by periodically analyzing the doughs for tyrosine bond level. Preferably wheat flours are analyzed by derivatizing the amino acids therein and measuring derivatized tyrosine content. In the case of dough analyses, the dough samples are periodically fluorometrically analyzed to determine tyrosine bond levels therein. Such data is then compared with preestablished standards and modifying additives such as oxidizing agents or free tyrosine can be added to adjust the tyrosine bond formation rate and tyrosine bond content of the dough.

14 Claims, 10 Drawing Sheets

Tyrosine Bonds Detected by Fluorescence

Tyrosine Bonds Detected by Fluorescence

Derivatized Dityrosine Reference Standard

Derivatized Tyrosine Bonds Detected by Fluorescence

Derivatized Tyrosine Bonds Detected by Fluorescence

Fluorescent Compounds Present in a Flour Sample

Fluorescent Compounds of a Dough Sample

Fluorescent Compounds Present in a Flour Sample

Fluorescent Compounds in a Dough in the Presence of 1% Free Tyrosine After One Minute of Mixing Fluorescent Compounds in a Dough in the Presence of 1% Free Tyrosine After Five Minute of Mixing Fluorescent Compounds in a Dough in the Presence of 1% Free Tyrosine After Ten Minute of Mixing Control Dough and Dough with 1% Free Tyrosine Added After Ten Minutes of Mixing

METHOD OF DOUGH MANUFACTURE BY MONITORING AND OPTIMIZING GLUTEN PROTEIN LINKAGES

BACKGROUND OF THE INVENTION

1. Field of the Invention

The present invention relates to the field of dough manufacture. More particularly, the invention is concerned with assessing flour samples for dough forming potential, monitoring subsequent dough formation and modifying the physical properties of the dough during the course of dough mixing. In practice, the levels of tyrosine, dityrosine and other tyrosine bonded compounds are measured in flour to predict dough forming properties, based on the potential level of tyrosine bonds that may be produced during mixing of the flour with water to produce a dough. The actual levels of bonds incorporating tyrosine formed in dough during mixing may also be monitored and manipulated as needed by the addition of oxidizing/reducing agents or tyrosine analogues to consistently produce high quality doughs.

2. Description of the Prior Art

In flour dough manufacture, dough is produced by mixing wheat flour and water. Other ingredients (e.g. salt) are added depending on the product being made. Dough made from wheat flour has a viscoelastic property not exhibited by doughs made from other cereals. This viscoelastic property is believed to be derived from gluten protein. The glutenin subunits, one of the two classes of storage proteins which are part of the gluten complex in wheat, are known to directly affect dough formation and bread making quality. Present theories regarding dough formation were developed with the idea that only disulfide crosslinks are involved in the mechanism of gluten structure formation. It was believed that these disulfide bonds were formed and/or broken and reformed during the mixing process and were ultimately responsible for the characteristics exhibited by a particular sample of dough.

Based on the intended use of the dough, different properties may be desired, i.e., a dough intended to be used for bread may have different desirable properties than a dough made for breakfast cereal processing. Additionally, similar flours used in dough processing may exhibit different characteristics during mixing due to environmental conditions present when the grain used to make the flour was growing or genetic differences. As can be seen, dough manufacture is affected by many different variables and it was heretofore impossible to predict with reasonable accuracy the qualities that any dough will exhibit during mixing based on an a priori analysis of the flour or wheat used.

The addition of oxidizing/reducing agents, metal chelating agents, or adjusting the dough pH during processing can affect the properties and consistency of the dough as desired. For example, a common modifier and improver of doughs, potassium bromate, has been determined to be potentially carcinogenic at certain levels and its use in bread doughs has been banned in the United Kingdom, Japan and New Zealand. The United States has limited the use of potassium bromate with maximum permitted levels of 50 or 75 ppm. However, following a request from the FDA in 1991, a majority of baking companies have voluntarily stopped using potassium bromate.

As a result of processing, dough can become sticky and reduce operating efficiency causing expensive delays and product loss. Alternatively, the dough can be overdeveloped or overworked resulting in low quality products. There is a point in time during mixing of every dough where continued mixing beyond that point results in a dough of inferior quality. Stopping the mixing process prior to that point also results in unacceptable dough quality. What is needed are methods of assessing dough forming potential of a flour prior to processing in order to precalibrate processing equipment thereby reducing the amount of manipulation required to efficiently produce an optimum dough; monitoring dough formation during processing so as to assess dough characteristics in a way that consistently results in product optimization; and manipulating dough formation during processing to effect optimization of the final dough product.

SUMMARY OF THE INVENTION

The present invention solves the prior art problems mentioned above and provides a distinct advance in the state of the art. In particular, through use of the methods of the present invention, an optimum flour dough product may be consistently prepared despite differences in initial flour quality or mixing times which previously resulted in doughs of dramatically different quality. Overall quality control in dough processing can be more tightly controlled through use of the methods of the present invention. The invention is predicated on the discovery that the content of bonds incorporating tyrosine residues in a dough (or the starting flour used in the dough) has a profound and heretofore unrecognized effect on dough manufacture and ultimate quality.

As used herein, the following definitions will apply: "tyrosine" refers to the tyrosine residues within a peptide or protein chain; "tyrosine bonds" refers to bonds between a tyrosine residue within a peptide or protein chain and another chemical moiety, free or within a polypeptide, and embraces dityrosine species as well as multiple bonds between respective tyrosine residues and a common bridging moiety; "free tyrosine" refers to the amino acid tyrosine when not within a peptide or protein chain; "dityrosine species" refers to two or more tyrosine residues within the same or different peptide or protein chains which are bonded together; "optimum" with respect to a dough's viscoelastic properties refers to when a dough exhibits desired physical characteristics based on the dough's eventual end-use taking into account the fact that doughs having different eventual end-uses may have different desired viscoelastic characteristics; and "analysis" with respect to tyrosine content refers to any technique for determining tyrosine content such as amino acid analysis of protein or protein hydrolysates, elucidation and analysis of appropriate nucleic acid sequences, and any other physical analytical methods (e.g. NMR).

The preferred dough monitoring method includes preparing a dough in the normal fashion and monitoring tyrosine bond formation. Tyrosine residues can bond and/or form crosslinks between and among other chemical residues or moieties, e.g., tyrosine residues, quinones, hydroquinone, dihydroxyphenylalanine (DOPA), dopaquinone, semiquinones, glutathione (GSH), cysteine, catechols and various carbohydrates. Some of these compounds may also act as a bridge between tyrosine residues in proteins. Structures including tyrosine residues include dityrosine, isodityrosine, trityrosine and other potential structures involving covalent bonds between and among tyrosine residues as well as crosslinks between tyrosine residues and other compounds. Typical tyrosine-bonded chemical moieties found in flours or doughs may include other tyrosine residues, quinones, hydroquinone, dihydroxyphenylalanine (DOPA), dopaquinone, semiquinones, glutathione (GSH), cysteine, catechols and various carbohydrates as well as other structures which could form tyrosine bonds.

As noted above, the addition of oxidizing/reducing agents, metal chelating agents, free tyrosine or adjusting the dough pH during processing can affect the properties and consistency of the dough as desired. For any given process, predetermined standards for an optimum range of tyrosine bonds will govern the monitoring and any subsequent modification of tyrosine formation in the dough. The monitoring provides continuous feedback indicating the approximate range of tyrosine bonds at individual stages in the process. If there are too many tyrosine bonds, this information is used for example to direct the addition of a specific amount of the amino acid tyrosine or metal chelating agents to the dough to prevent over-formation of tyrosine bonds. If this factor is not monitored or tyrosine is not added, continued mixing will cause the dough to become too sticky resulting in an obstruction of the machinery and ultimately, product waste. The present invention also allows for mixing to progress past the point in time at which, the dough has an optimum number of tyrosine bonds and the dough exhibits desired viscoelastic properties. If free tyrosine is added to the dough once an optimum range of tyrosine bonds is reached, mixing may continue without a significant subsequent increase in the number of tyrosine bonds and corresponding loss of desired viscoelastic properties. This occurs due to an inhibition of tyrosine residues within the protein or peptide chains binding with other tyrosine residues within the protein or peptide chains brought about by the added free tyrosine occupying the binding sites of the tyrosine residues within the protein or peptide chains. Thus, mixing may continue without a significant corresponding increase in tyrosine bonds and loss of desired viscoelastic properties. Preferably, mixing may continue for up to about 10 minutes after reaching the optimum range of tyrosine bonds while retaining +/−10% of the desired viscoelastic properties. More preferably, mixing may continue for up to about 20 minutes after reaching the optimum range of tyrosine bonds while retaining +/−10% of the desired viscoelastic properties. Still more preferably, mixing may continue for up to about 10 minutes after reaching the optimum range of tyrosine bonds while retaining +/−20% of the desired viscoelastic properties. Even more preferably, mixing may continue for up to about 20 minutes while maintaining +/−20% of the desired viscoelastic properties. Increasing the pH of the dough will also result in a decrease in the rate of dough formation and may decrease the rate of tyrosine bond formation. Conversely, if there are not enough tyrosine bonds at a given stage of the mixing process, oxidizing agents may be added which may increase the rate of tyrosine bond formation. This will increase dough quality by causing development of necessary viscoelastic properties. Additionally, decreasing the pH of dough during processing will also affect dough characteristics and may promote tyrosine bond formation.

The preferred method would also include using a computer program configured to achieve a predetermined range of tyrosine bonds in a dough by directing the manipulation and/or addition of additives to the dough during mixing. These steps would be carried out manually or automatically in response to the approximate number of tyrosine bonds found by analysis at any stage in the process. Any suitable analytical procedure could be followed, for example, fluorescence detection. Following such analyses, the dough could be modified by the addition of the appropriate tyrosine bond formation modifier such as oxidizing agents, metal chelating agents, free tyrosine, and pH adjustment. Also, the physical mixing of the dough could be altered as necessary. This procedure could be carried out stepwise until the range of tyrosine bonds is within a predetermined range for a given dough application.

Additionally, the starting flour used to make the dough may be screened to predict the dough forming potential for a particular use prior to initiating any mixing. This screening is done in much the same way as the monitoring of dough during mixing. In this method, the approximate levels of tyrosine and/or tyrosine bonds in a flour sample are measured in order to assess and predict the dough forming potential based on the respective native, naturally occurring amounts of these compounds. Preferably the flour is analyzed to determine the amount of tyrosine therein because the amounts of tyrosine bonds therein is usually very small. The analysis is normally accomplished by measuring the content of tyrosine in the flour. This provides the advantage of a screening technique that is more sensitive than the on-line technique method of analyzing the tyrosine bonds during dough manufacture. Knowledge of the tyrosine and tyrosine bond content of the storage proteins (glutenin and gliadin) in flour to be used in the dough forming process can reduce the amount of on-line manipulation needed to produce an optimum dough for a particular use and allows the operators of the machinery used in dough manufacture to precalibrate their mixing apparatus thereby facilitating production of an optimum dough with a minimum of manipulation.

Finally, analysis of the approximate levels of tyrosine and/or tyrosine bonds in a wheat flour sample contributes to a method of "grading" wheat and/or flour. Flours may be grouped according to the levels of tyrosine and/or tyrosine bonds found within the storage protein chains. It is believed that the glutenin subunits of the gluten protein chains occupy a more significant role with respect to a dough's viscoelastic properties, however, the gliadin subunits may still be of importance with respect to tyrosine bonds and their effect on a dough's physical characteristics. Flours having tyrosine and/or tyrosine bond levels falling within a certain range would be grouped together and designated as having a certain grade. The grade would therefore indicate the approximate range of tyrosine and/or tyrosine bonds inherent in the flour. This would allow users of flour for different applications to choose a flour that has a desired starting amount of tyrosine and/or tyrosine bonds which would contribute to the consistent production of high quality end products.

DETAILED DESCRIPTION OF THE PREFERRED EMBODIMENT

The following examples set forth preferred embodiments of the present invention. It is to be understood, however, that these examples are provided by way of illustration and nothing therein should be taken as a limitation upon the overall scope of the invention.

EXAMPLE 1

Materials and Methods

Samples of wheat dough consisting of wheat flour and deionized water were taken during mixograph analysis at one, five, ten, fifteen, and twenty minutes after mixing began. The mixograph method of the American Association of Cereal Chemists (AACC), method 54-40A, was used and is hereby incorporated by reference. Protein was extracted from these samples with 70% ethanol for one hour and then dialyzed. The samples were vacuum dried and submitted for amino acid analysis. The amino acid analysis protocol utilized has been previously described by Malencik et al., 184 Anal. Biochem., 353–359 (1990), the teachings of which are herein incorporated by reference. The dityrosine used as a reference standard for bonds between tyrosine residues was obtained from the Department of Biochemistry and Biophysics, Oregon State University.

Results

Figure 1:
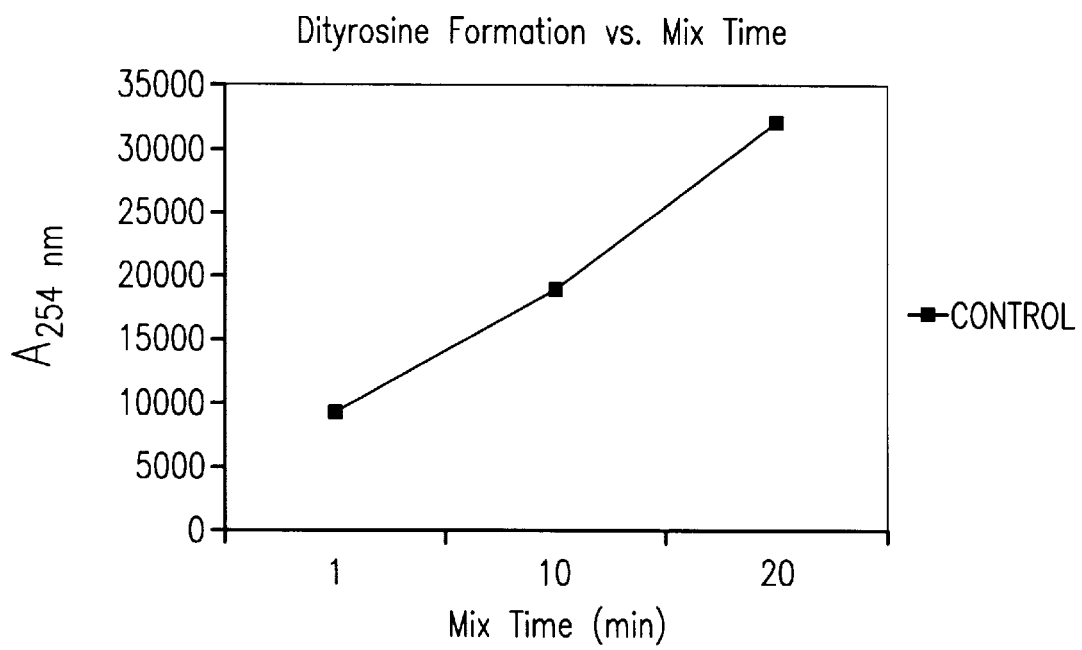
FIG. 1 is a graph illustrating the increase of tyrosine bonds over time during mixing of a dough.

It was determined that the number of tyrosine bonds between tyrosine residues increased steadily during the mixing process. This indicates that bonds between tyrosine residues of gluten proteins are forming during the mixing process. It is believed that the glutenin subunits of the gluten protein chains occupy a more significant role with respect to this increase of tyrosine bonds, however, the gliadin subunits may still be of importance with respect to the increase in tyrosine bonds. As shown in FIG. 1, this steady increase of tyrosine bonds resulted in an increase in the signal detected (absorbance at 254 nm) in the peak representing the tyrosine bond, dityrosine, between one minute of mixing and 20 minutes of mixing. The dough in the experiment began as a regular mixture of wheat flour and deionized water, progressed during mixing to a good quality dough and proceeded to lose its elasticity and become too sticky, eventually proceeding to breakdown as mixing progressed. This data indicates that dough formation in the early stages of mixing and "breakdown" of dough during mixing after peak development are caused by the formation of tyrosine bonds. There does not appear to be any breaking of covalent bonds, but simply the accumulation of tyrosine bonds as mixing continues. This "breakdown" was conventionally thought to be the breaking of covalent bonds (the disulfide bonds) but now appears to be the result of overformation of tyrosine bonds by the crosslinking of tyrosine residues such that the dough has lost its elastic nature and the mixograph trace appears to be "breaking down".

EXAMPLE 2

Samples of wheat dough consisting of wheat flour and deionized water were taken during mixograph analysis at one, five, ten, fifteen, and twenty minutes after mixing began. Prior to mixing, a solution of 5% ascorbic acid was added to the system. Protein was extracted from these samples with 70% ethanol for one hour and then dialyzed. The samples were vacuum dried and submitted for amino acid analysis. The amino acid analysis protocol utilized in example 1 was utilized in this example. The dityrosine used as a reference standard for tyrosine bonds between tyrosine residues was obtained from the Department of Biochemistry and Biophysics, Oregon State University.

Results

Figure 2:
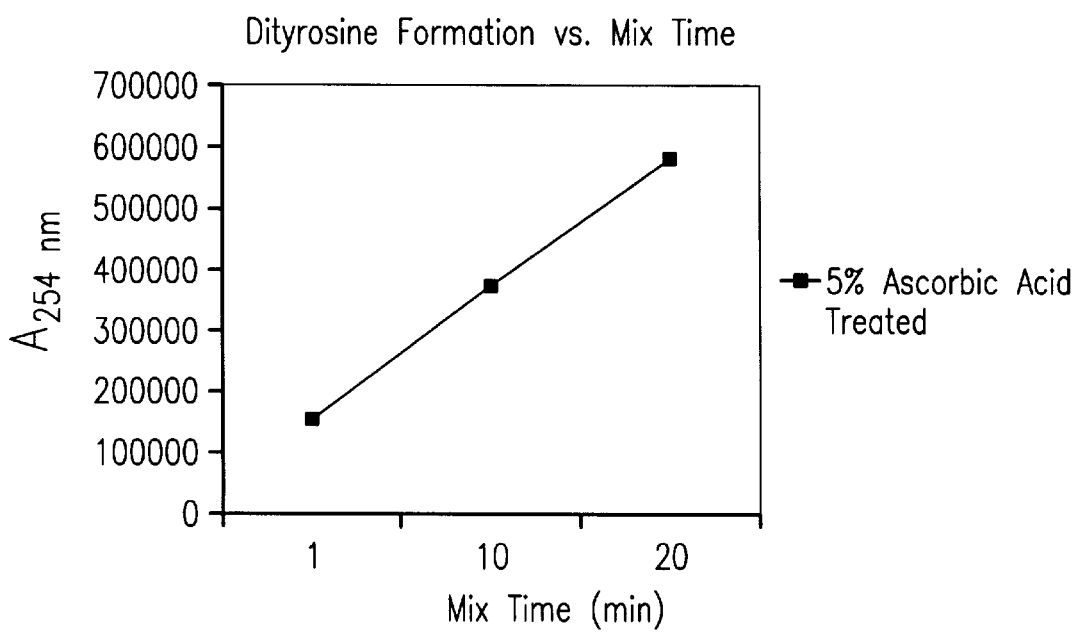
FIG. 2 is a graph illustrating the effect of ascorbic acid on tyrosine bond formation during mixing of a dough.

The results of example 2 are illustrated in FIG. 2. Levels of signal detected (absorbance at 254 nm) in the peak representing the tyrosine bond, dityrosine, are much greater than the levels in the control mixograph (FIG. 1) and the formation of tyrosine bonds increases as mixing progresses at a greater rate than in the control mixograph. These results indicate that tyrosine bond formation is enhanced with the addition of agents such as ascorbic acid and these may in turn be used to contribute to modifying the dough forming process in order to provide improved dough based products.

EXAMPLE 3

Materials and Methods

This experiment compared tyrosine formation consisting of crosslinks among tyrosine residues between control wheat flour, control wheat flour with 1% (w/v) aqueous free tyrosine added and control wheat flour with 1% (w/v) aqueous free phosphotyrosine added. A dough was prepared by mixing each of the respective flour samples with deionized water. For the samples containing the free tyrosine and free phosphotyrosine, these two latter ingredients were present in the water added to the control flour to produce the dough. Results of this example are given in FIGS. 3, 4 and 5.

Results

Figure 3:
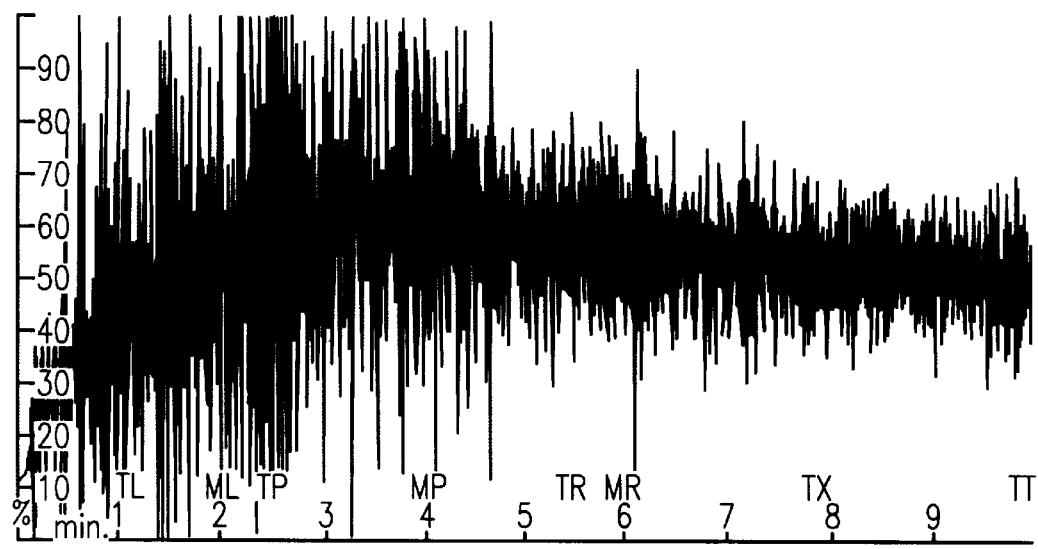
FIG. 3 is a graph illustrating a control mixograph during dough mixing.

The mixograph results from the control wheat flour dough are given in FIG. 3. The line marked MP means midline mixing peak and is the point at which the dough is mixed to optimum for breadmaking properties. The lines marked ML and MR indicate points along the midline curve either 2 minutes to the left (ML) or 2 minutes to the right (MR) of the MP. The line marked TP is the envelope mixing peak. "Envelope" refers to the two lines seen, one outlining the top of the curve and the other outlining the bottom of the curve. The peak of the top line is the highest point on it. The lines marked TL and TR are just indicating points on the upper envelope curve either to the left (TL) or right (TR) of the envelope mixing point (TP). The line marked TX is an arbitrary time set for data collection that was set at 8 minutes in this case in order to determine the width of the curve two minutes prior to the end of the analysis. The line marked TT refers to curve tail and refers to the end of the analysis.

Figure 4:
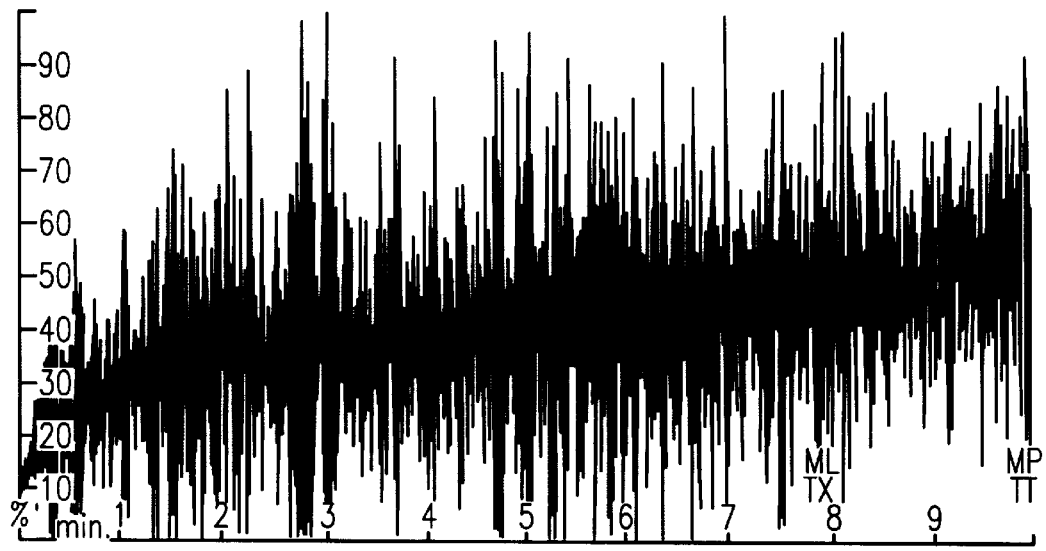
FIG. 4 is a graph illustrating the effect on dough formation by adding free tyrosine during mixing.
Figure 5:
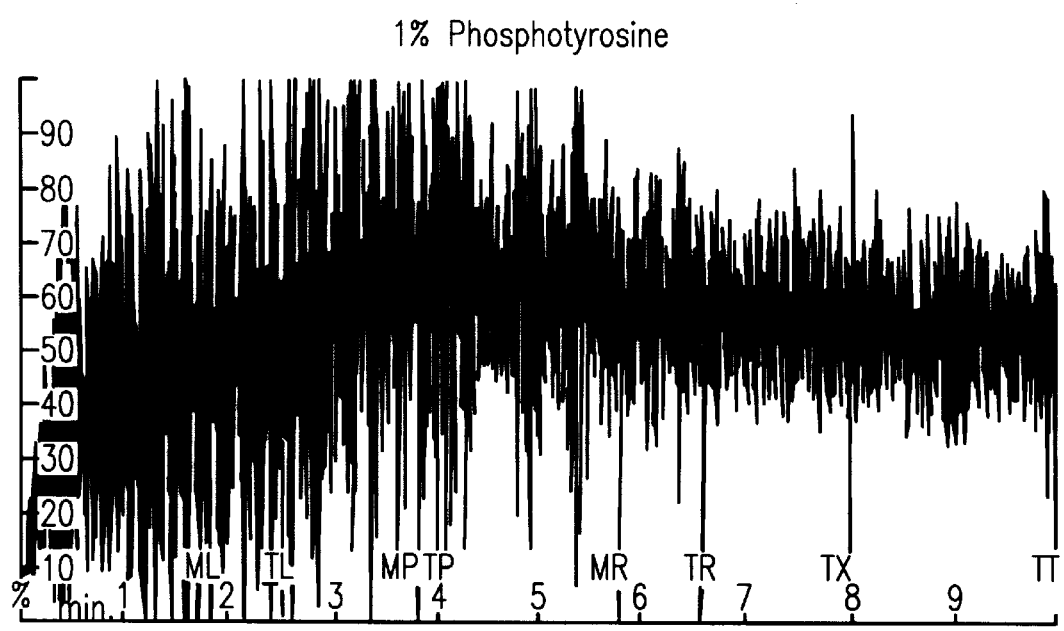
FIG. 5 is a graph illustrating the effect of adding phosphotyrosine during mixing of a dough.

Mixograph analyses illustrated in FIG. 4 were performed with free tyrosine incorporated in the deionized water and produced mixograms that did not "break down". In other words, they appeared to have extended tolerance to mixing. These results indicate that the free tyrosine was becoming associated or bonded with the tyrosine within the storage protein structure (mainly in the glutenin subunits) thereby preventing the crosslinking between tyrosine residues within the storage proteins. When compared to the mixograph shown in FIG. 3, it is apparent that the optimum mixing point (TP) is not reached as quickly when free tyrosine is added. ML, TX and TT are also indicated on this mixograph.

In comparison, mixograph analyses performed with phosphotyrosine (shown in FIG. 5) incorporated in the water exhibited properties substantially similar to those obtained with the control flour (shown in FIG. 3) in that they experienced "breakdown". This indicates that the phosphorylated tyrosine does not interact with the tyrosine residues in the storage proteins as free tyrosine does. Bonding of tyrosine through crosslinking between tyrosine residues occurs in the same manner in which it does during the mixing of control flour. As in FIG. 3, lines corresponding to ML, MR, TL, TR, IX and TT are also indicated.

EXAMPLE 4

Materials and Methods

Three 64 $\mu$g dough samples consisting of wheat flour and deionized water were taken at zero, five and ten minutes after mixing began. Each sample was analyzed by direct amino acid analysis with fluorescence detection to determine the level of tyrosine bonds consisting of links between tyrosine residues present in each sample. The samples were hydrolyzed and amino acid analysis by HPLC was performed on the underivatized samples. Tyrosine bonds consisting of cross-links between tyrosine residues fluoresce when excited at a wavelength of 285 nm and emit light at 405 nm, therefore analyses of the amino acids obtained from dough samples were analyzed under these conditions with a fluorescence detector (a fluorometer). All samples were compared to the dityrosine used as a reference standard which eluted at 18.995 minutes.

Results

Figure 6:
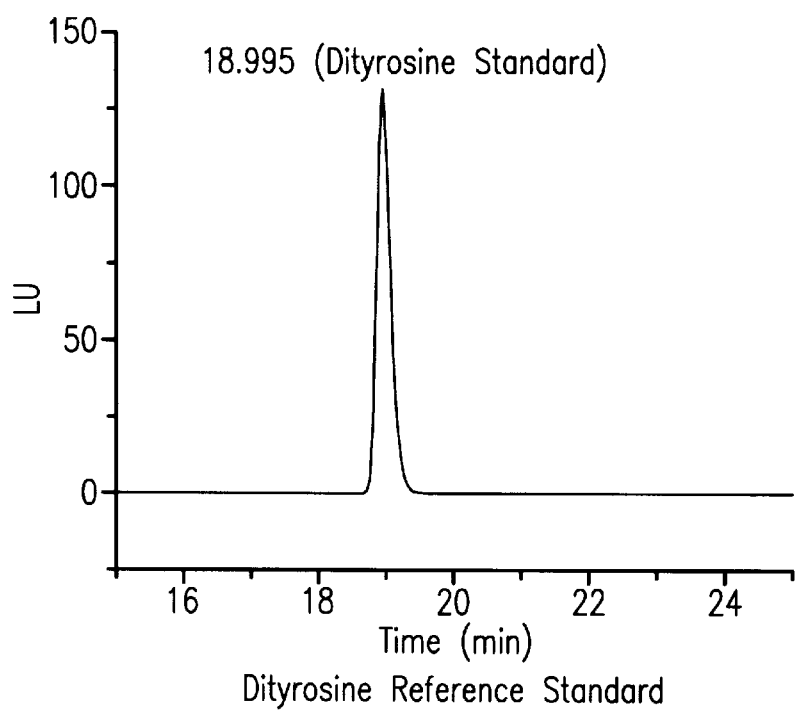
FIG. 6 is a graph illustrating dityrosine used as a reference standard detected by fluorescence.
Figure 7:
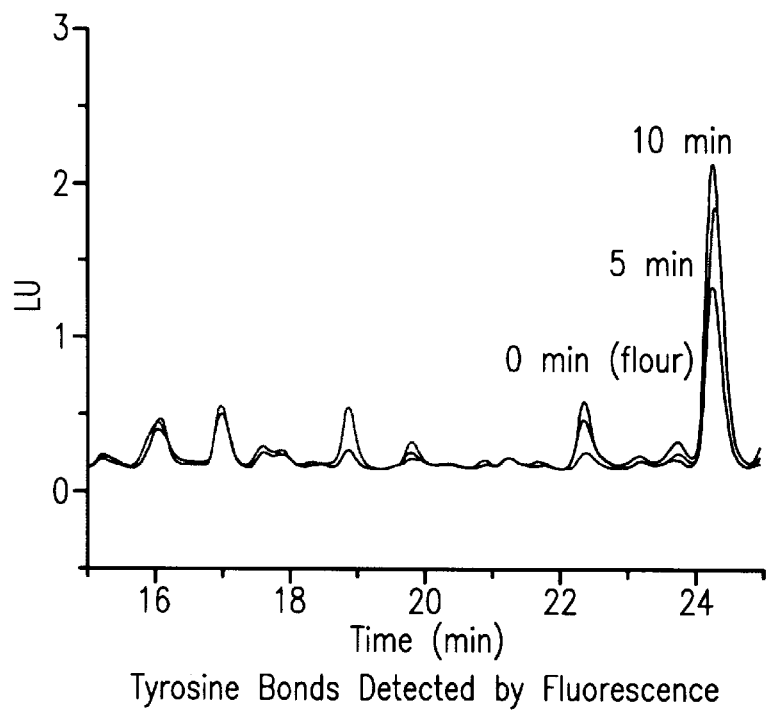
FIG. 7 is a graph illustrating the amount of tyrosine bonds present in a flour sample and dough samples mixed for five and ten minutes, respectively, detected by fluorescence.

FIG. 6 shows the dityrosine used as a reference standard eluting at 18.995 minutes. FIG. 7 shows the amino acids present in a flour sample compared with dough samples that were mixed for five and ten minutes. Five minutes of mixing was near the optimum mixing point of this flour sample and therefore may represent the "ideal" number of these tyrosine bonds necessary for baking purposes. There is an easily detectable amount of tyrosine bonds formed at this point in mixing as is evidenced by the peak at 18.896 minutes in the chromatogram.

FIG. 7 also shows the amino acids present in the dough sample that was mixed for ten minutes. Again, the tyrosine bond peak at 18.896 minutes has increased. This level of tyrosine bond formation is probably indicative of an over-formation of tyrosine bonds. The dough has now been mixed beyond its ideal for baking purposes. This sample was taken at a point in mixing that cereal chemists refer to as "breakdown" because the dough does not retain its resistance to extension and is not as elastic as it would be after only five minutes of mixing.

All of these results demonstrate that tyrosine bonds increase steadily during the dough mixing process and are detectable by direct analysis with a fluorescence detector. This is critical because on-line analysis during dough processing is dependent upon direct analysis of the dough while it is in the mixer in order to give timely feedback regarding tyrosine bond formation such that appropriate steps may be taken to manipulate these levels in the dough. This data also demonstrates that tyrosine bond formation occurs continuously during mixing.

EXAMPLE 5

Material and Methods

Samples of wheat flour were taken to determine the approximate level of tyrosine bonds therein prior to forming any dough. Knowledge of the amount of tyrosine bonds present in the flour provides an indication of the crosslink forming potential of a flour sample. It may also indicate the types or extent of modifications that may be necessary in order to produce an optimum dough product. The samples were hydrolyzed and amino acid analysis by HPLC was performed on the underivatized samples. The amino acids were then analyzed with fluorescence at a wavelength of 285 nm and compared to the dityrosine used as a reference standard which eluted at 19.579 minutes. The amino acid analysis protocol utilized in example 4 was utilized in this example. The tyrosine bond standard was obtained from the Department of Biochemistry and Biophysics, Oregon State University.

Results

Figure 8:
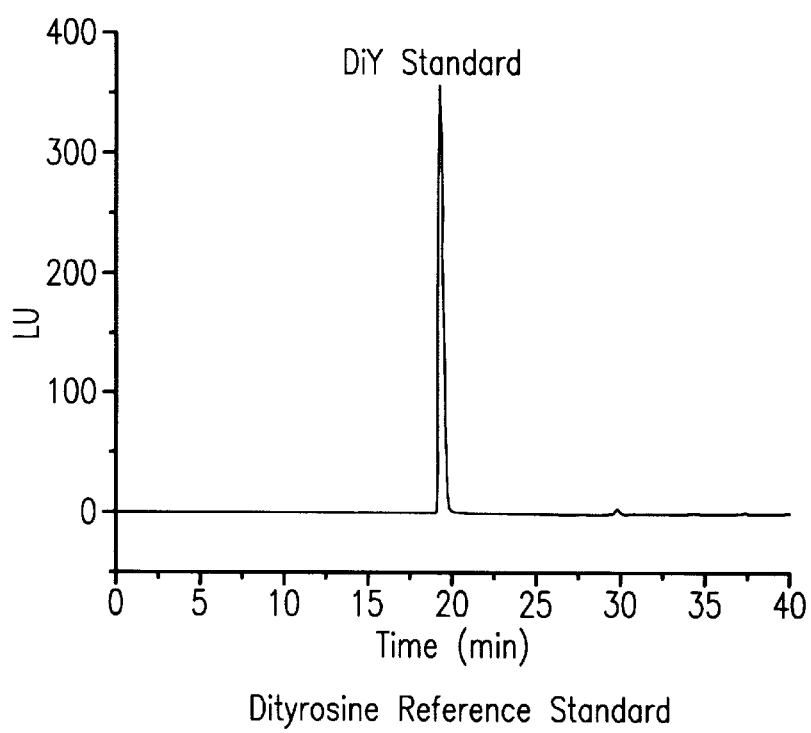
FIG. 8 is a graph illustrating dityrosine used as a reference standard detected by fluorescence.
Figure 9:
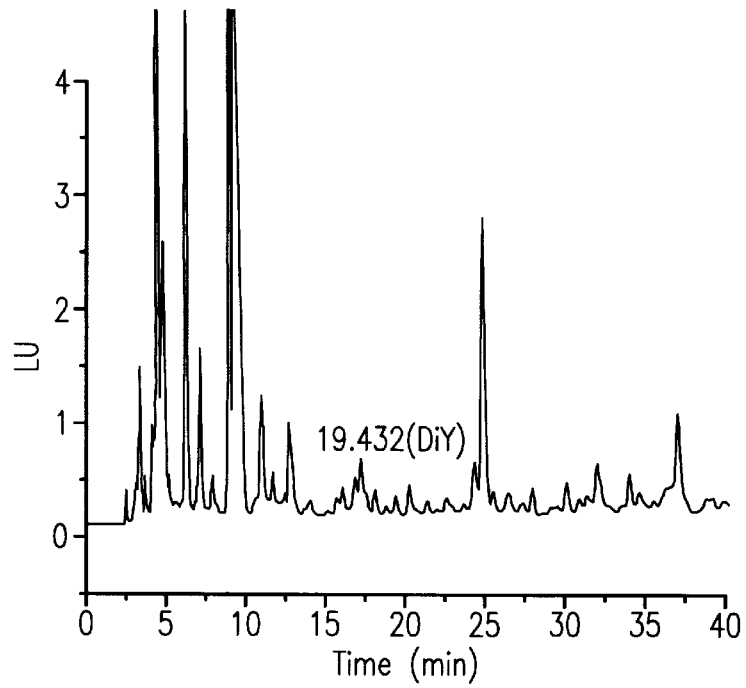
FIG. 9 is a graph illustrating the amount of tyrosine bonds detected by fluorescence in a sample of flour.

The approximate amount of tyrosine bonds in flour samples was determined using fluorescence detection. FIG. 8 illustrates the tyrosine bond standard eluting at 19.579 minutes. FIG. 9 illustrates the approximate amount of tyrosine bonds present in a sample of flour as detected by fluorescence. The peak at 19.432 minutes represents approximately 83 pmol of tyrosine bonds/,ug of protein. The tyrosine bond level can then be used to predict the rate at which tyrosine bonds would be formed during the mixing of a dough as well as predicting the amount and type of manipulation that may be needed to consistently produce an optimum dough product. For example, if the flour exhibited a low level of tyrosine bonds (as compared to a control sample standard), the operator of the machinery used to produce a dough would know that a longer mixing time and/or the addition of oxidizing agents would be necessary to produce an optimum dough product. This would also allow any automated machinery to be precalibrated such that the initial tyrosine bond content of the flour would be taken into account when programming mixing times and ingredient additions.

Figure 10:
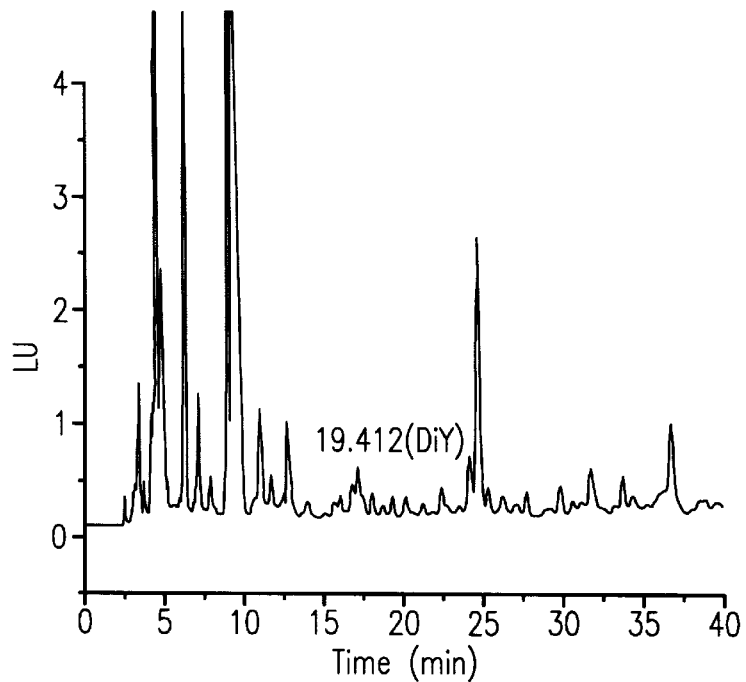
FIG. 10 is a graph illustrating the amount of tyrosine bonds detected by fluorescence in a second sample of flour.

Similarly, FIG. 10 illustrates the approximate amount of tyrosine bonds present in a second flour sample. The peak at 19.412 minutes represents approximately 105 pmol of tyrosine bonds/$\mu$g of protein.

EXAMPLE 6

Material and Methods

Samples of the flour used in Example 5 were hydrolyzed and subsequently derivatized and HPLC analysis was performed on these derivatized amino acids. The derivatiztion procedure of Cohen and Michaud, Anal. Biochem., 211, 279–287 (1993) was used. This procedure is hereby incorporated by reference.

Results

Figure 11:
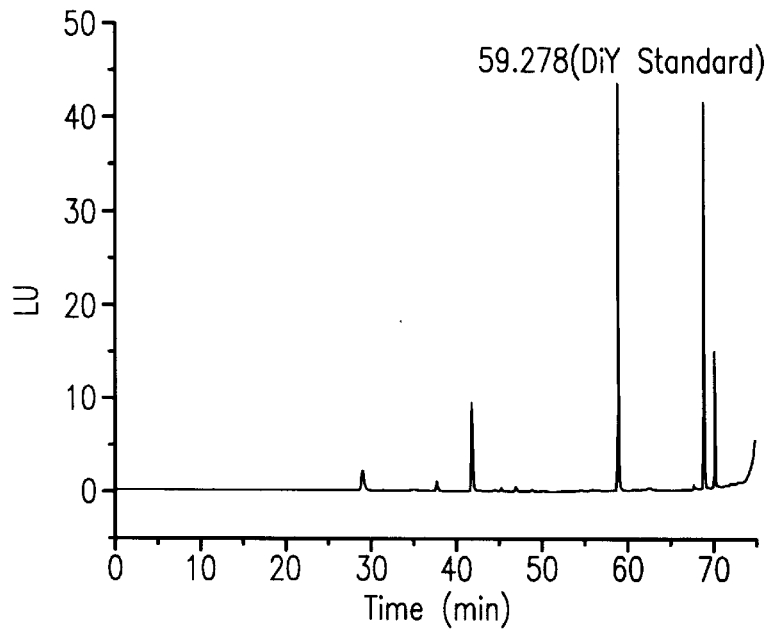
FIG. 11 is a graph illustrating the derivatized dityrosine used as a reference standard detected by fluorescence.
Figure 12:
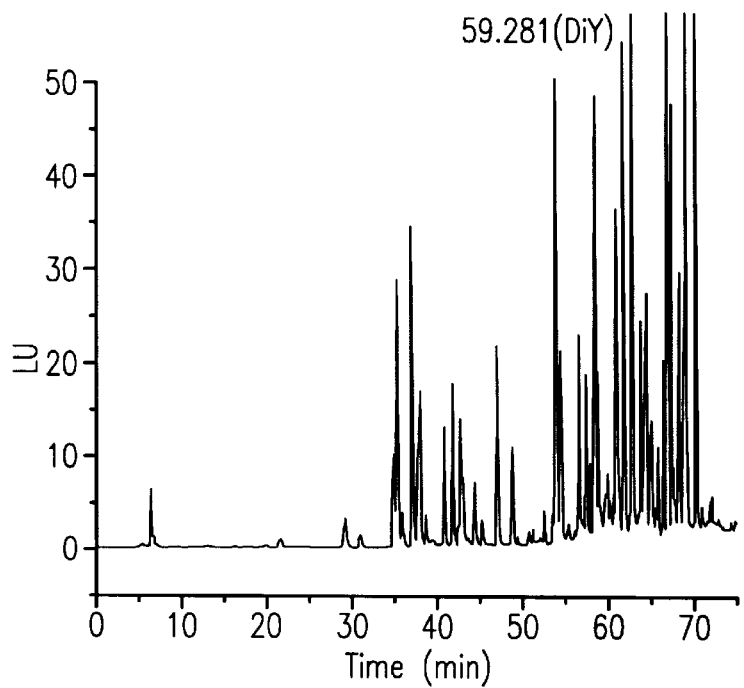
FIG. 12 is a graph illustrating the amount of tyrosine bonds detected by fluorescence in a sample of derivatized amino acids from a flour sample.
Figure 13:
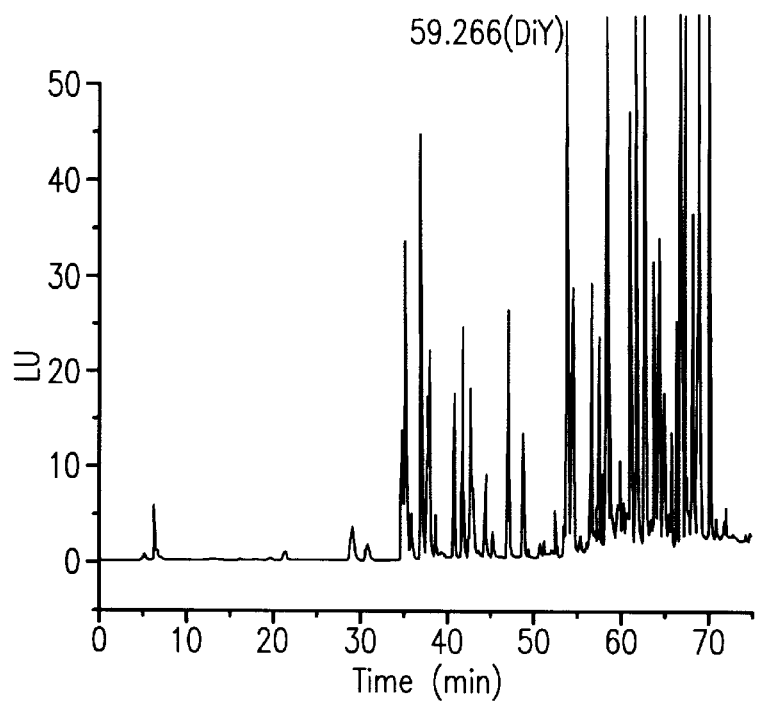
FIG. 13 is a graph illustrating the amount of tyrosine bonds detected by fluorescence in a sample of derivatized amino acids from a second flour sample.

Testing on the derivatized amino acids allowed detection of even very low levels of tyrosine bonds. Due to the sensitivity of this testing, it is a preferred method for analyzing flour and predicting tyrosine bond forming potential based on the amount of tyrosine and tyrosine bonds present in the sample. FIG. 11 shows the derivatized dityrosine standard eluting at 59.278 minutes. FIG. 12 illustrates the derivatized tyrosine bonded species from the first sample eluting at 59.261 minutes. The area under the peak represents approximately 83 pmol of tyrosine bonds/µg of protein. FIG. 13 illustrates the derivatized tyrosine bonded species from the second sample eluting at 59.266 minutes. The area under that peak represents approximately 105 pmol of tyrosine bonds/µg of protein. As is apparent from these two samples, flours may inherently have varying amounts of tyrosine bonds. The actual amount of tyrosine and tyrosine bonded species present in a given flour may correlate to the tyrosine bond forming potential of the flour during dough processing. Thus, measuring the initial content of tyrosine and tyrosine bonded species of the starting flour and thereafter measuring and controlling/manipulating the tyrosine and tyrosine bonded species in the dough during processing will result in higher quality end products with decreased waste.

EXAMPLE 7

Material and Methods

This experiment demonstrated that tyrosine residues were linking with several components in flour and forming fluorescent compounds. First, a sample of flour was analyzed using HPLC followed by fluorescence detection. Results from this sample are given in FIG. 14. Dough samples that had been mixed for ten minutes were then analyzed to determine whether other compounds were incorporated into bonds with tyrosine. The sample was analyzed using HPLC followed by fluorescence detection. The results from this sample were compared to the flour sample.

Results

Figure 14:
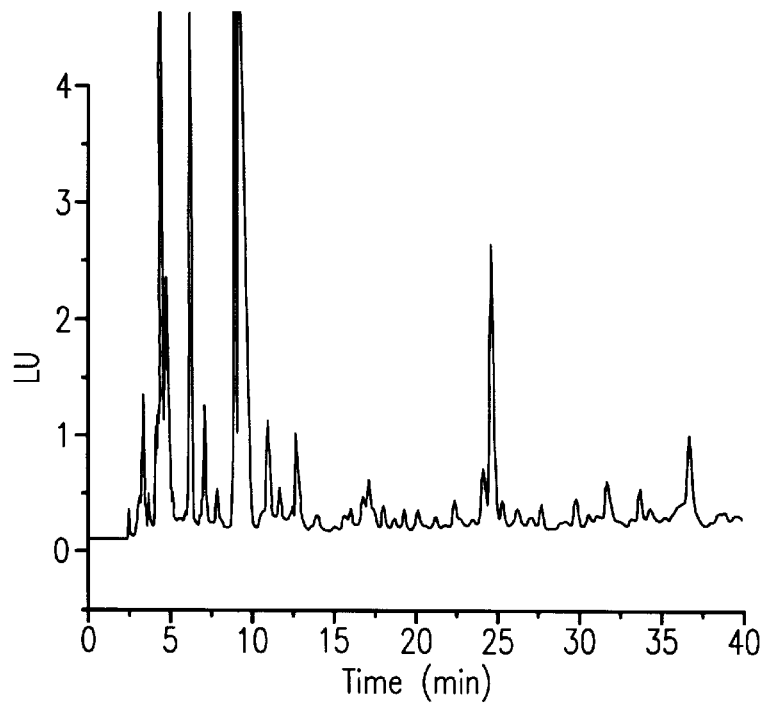
FIG. 14 is a graph illustrating the fluorescent compounds present in a sample of flour.
Figure 15:
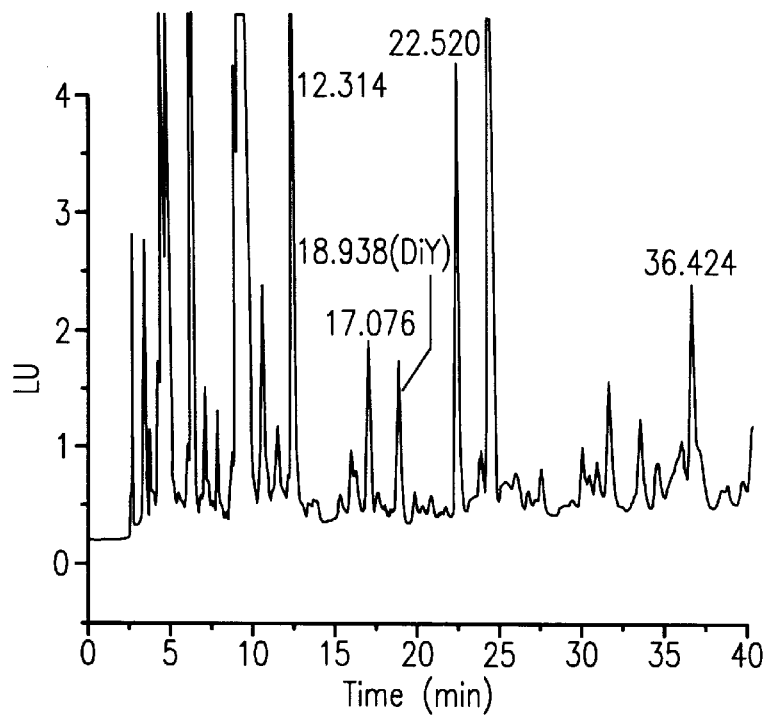
FIG. 15 is a graph illustrating the fluorescent compounds present in a dough mixed for ten minutes.

FIG. 14 shows the results of the flour sample and FIG. 15 shows the results of the dough sample. In FIG. 15, other bonds incorporating tyrosine are evident by the peaks at 12.314 minutes, 17.076 minutes, 22.520 minutes and 36.424 minutes. The tyrosine bond peak at 18.938 represents dityrosine. This shows that other bonds incorporating tyrosine are also being formed during the mixing process which may also affect dough forming characteristics. When combined with the knowledge of the starting tyrosine content, the rate and/or potential for forming bonds incorporating tyrosine could be predicted.

EXAMPLE 8

Materials and Methods

Figure 17:
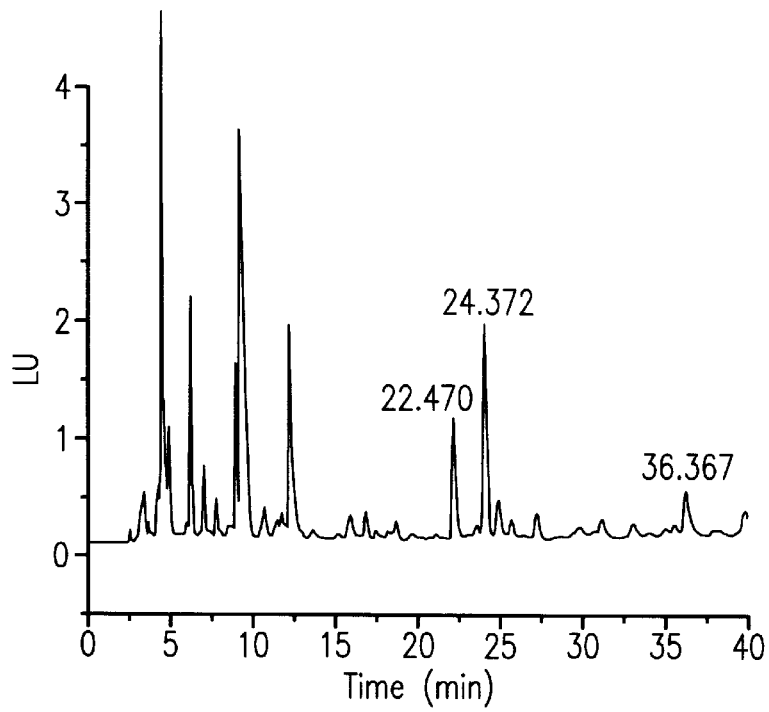
FIG. 17 is a graph illustrating the fluorescent compounds including tyrosine present in a dough sample after one minute of mixing in the presence of an additional 1% free tyrosine.
Figure 18:
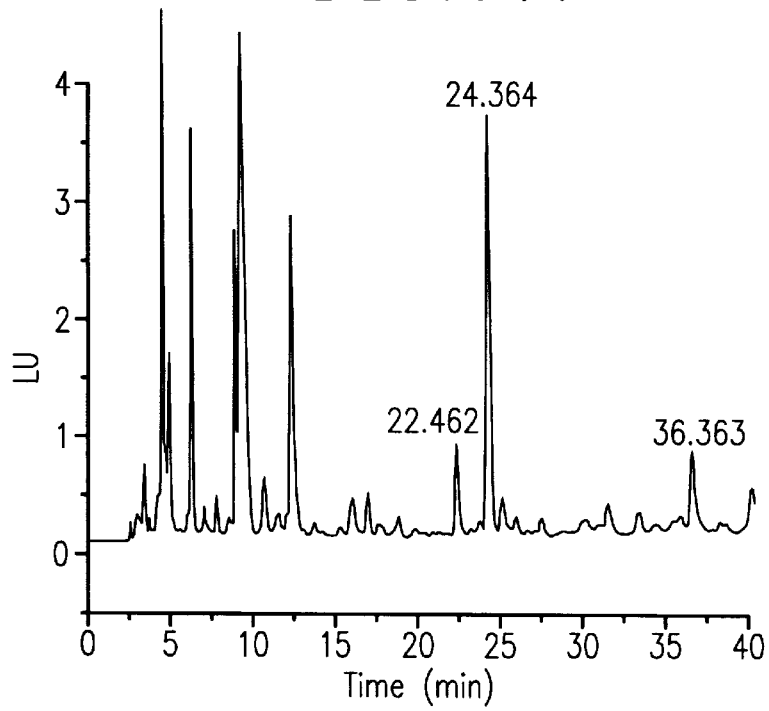
FIG. 18 is a graph illustrating the fluorescent compounds including tyrosine present in a dough sample after five minutes of mixing in the presence of an additional 1% free tyrosine.
Figure 19:
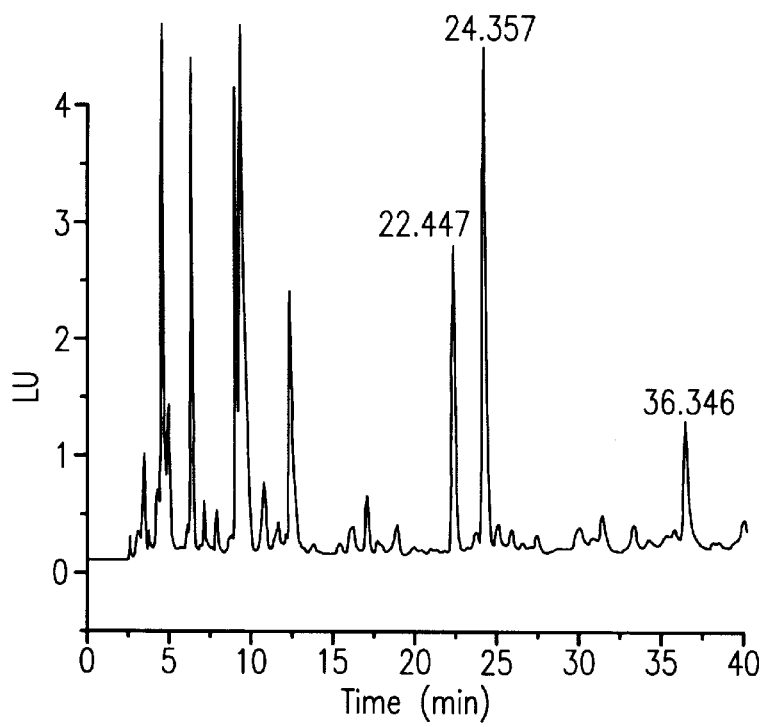
FIG. 19 is a graph illustrating the fluorescent compounds including tyrosine present in a dough sample after ten minutes of mixing in the presence of an additional 1% free tyrosine.

This experiment tested the effects of adding 1%(w/v) aqueous solution of free tyrosine to flour to make a dough. Samples of the dough were taken at one, five and ten minutes. These samples were hydrolyzed and HPLC performed on the underivatized amino acids. The results were compared to each other and a sample of flour to see which peaks increased as mixing progressed. Results for the flour sample are given in FIG. 16 while the results for the dough samples are given in FIGS. 17, 18, and 19 respectively.

Results

As in Example 3, FIG. 4, doughs with 1%(w/v) free tyrosine added have an extended tolerance to mixing. These doughs did not fully form properly mixed doughs during mixograph analysis. The peaks representing tyrosine bonds consisting of bonds between and among tyrosine residues that appear at around 18.8 minutes in these chromatograms and others have almost disappeared. However, the peaks around 22.4 and 24.3 minutes increase dramatically in comparison to the same data from control doughs mixed to the same time but without having the addition of free tyrosine. This is evidence that the compounds of these peaks are incorporating most of the free tyrosine. The tyrosine bond peak at 18.8 minutes likely decreases because of the free tyrosine being preferentially incorporated into the structures that elute at 22.4 and 24.3 minutes respectively.

The addition of free tyrosine may also prolong mixing times once a predetermined range of tyrosine residues within the gluten storage protein chains have formed bonds. This is due to the free tyrosine bonding with the tyrosine residues within the protein or peptide chains thereby preventing them from forming crosslinks with other tyrosine residues within the protein or peptide chains. To maintain desired viscoelastic properties (consistency, stickiness, elasticity, etc.) beyond the conventional mixing point as determined by conventional mixograph analysis, a quantity of free tyrosine would be added once the range of tyrosine bonds reached a predetermined standard. This free tyrosine would inhibit further binding between tyrosine residues within protein or peptide chains allowing the mixing process to be extended without a change in the viscoelastic properties. Preferably, the mixing time could be extended for about 10 minutes in comparison to the optimum mixing time as determined by conventional mixograph analysis while maintaining +/−10% of the desired viscoelastic properties of the dough. More preferably, the mixing time could be extended for 20 minutes while maintaining +/−10% of the desired viscoelastic properties. Still more preferably, the mixing time could be extended for 20 minutes while maintaining +/−20% of the desired viscoelastic properties of the dough. Similar alterations of the mixing time and maintenance of desired viscoelastic properties of the dough may be accomplished using the other dough modifiers as discussed above.

EXAMPLE 9

Materials and Methods

Figure 20:
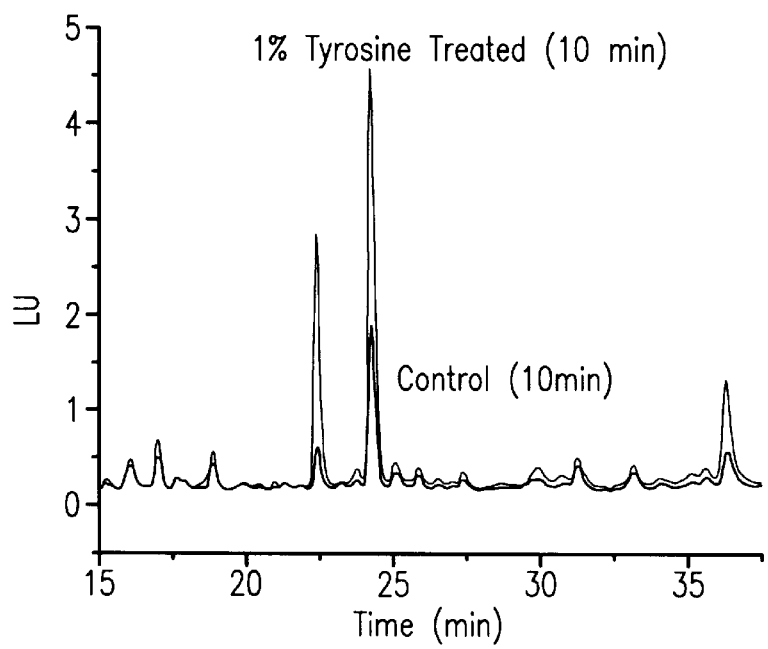
FIG. 20 is a graph comparing the peaks from a control dough mixed for ten minutes to a dough mixed for ten minutes with 1% free tyrosine added.

This example compared the peaks from a control dough that had been mixed for ten minutes to a dough with 1% free tyrosine added that had been mixed for ten minutes. The samples were hydrolyzed and HPLC analysis was performed on the underivatized amino acids. Results of this experiment are given in FIG. 20.

Results

Two peaks of interest are represented at 22.447 minutes and 24.557 minutes respectively. As is apparent, the dough with a 1%(w/v) aqueous solution of free tyrosine added has a much higher level of tyrosine bonds in these peaks than in the peaks of the control dough. This indicates that the free tyrosine is being incorporated into the compounds that are forming these peaks and affecting the characteristics of the dough. As in example 3, FIG. 4 and example 8, FIGS. 17, 18 and 19, the dough with 1% free tyrosine exhibited an extended tolerance to mixing.

EXAMPLE 10

Materials and Methods

This example illustrates one method of determining and setting the predetermined optimum range standard of tyrosine bonds for a given product or application utilizing these bonds. Finding the predetermined optimum standard for each application allows the producer of the product or machinery operator to compare the range or number of bonds present in a production run to that of an ideal product. This standard is found by producing the product under optimum processing conditions and taking samples at various stages of the production process. These samples would be analyzed to determine the approximate range of tyrosine bonds present in the sample at each stage. This could be done with an infinitely large number of samples at an infinitely large number of stages in the process (e.g. every minute, every second, every 1/10th of a second, etc.) in order to provide as narrow of a target or optimum range as possible. The range or number of tyrosine bonds found at each stage of the processing of ideal products would then be used as a benchmark to control future processing of that particular product. The number of tyrosine bonds found at each stage of processing would be compared to the optimum or ideal number for that stage and any necessary modifications could be made to bring the number of tyrosine bonds within the optimum range, thereby ensuring that an optimum product is made every time.

Preferably, this entire process would be done through a computer program configured to direct the processing of any product utilizing tyrosine bonds. For example, the preferred computer program would be designed to direct the operator of the equipment to either manually or automatically:

1) Direct random analyses of the material being processed in order to determine the approximate range of tyrosine bonds at that stage of the processing;
2) Compare the analyzed range found to the optimum range for that stage of the process;
3) Direct the modification of the product as necessary with any useful methods to bring the number of tyrosine bonds into the ideal range; and
4) Repeat as necessary or as often as desired for each run.

Results

Comparing the analyzed ranges from each production run with the predetermined ideal standard allows for the production of products that consistently exhibit optimum characteristics. Of course, the ideal range of tyrosine bonds will be more accurate if many samples are taken from many different production runs that result in ideal products. This method is useful for all products utilizing tyrosine bonds in that ideal ranges may be found and used to govern subsequent production of each product. Furthermore, the ideal range may be based on bonds between and among tyrosine residues or between tyrosine residues and other compounds (which may bridge storage protein chains or be storage protein chain substituents) such as quinones, hydroquinone, dihydroxyphenylalanine, dopaquinone, semiquinones, glutathione, cysteine, catechols and various carbohydrates (tyrosine bonds), all of which may be measured using the methods outlined in the examples above.

Other advantages deriving from the use of a predetermined standard are that modification of the number of tyrosine bonds found at a given stage during any production run based on the ideal range of tyrosine bonds that should be exhibited at that stage results in a subsequent reduction of product that does not meet quality control standards and therefore, a reduction in wasted product. This will also thereby reduce the operating costs associated with wasted product and standardize quality control. Moreover, the parameters controlling the modification of the number of tyrosine bonds can be easily changed should the ideal range ever need to be adjusted.

Discussion

Figure 16:
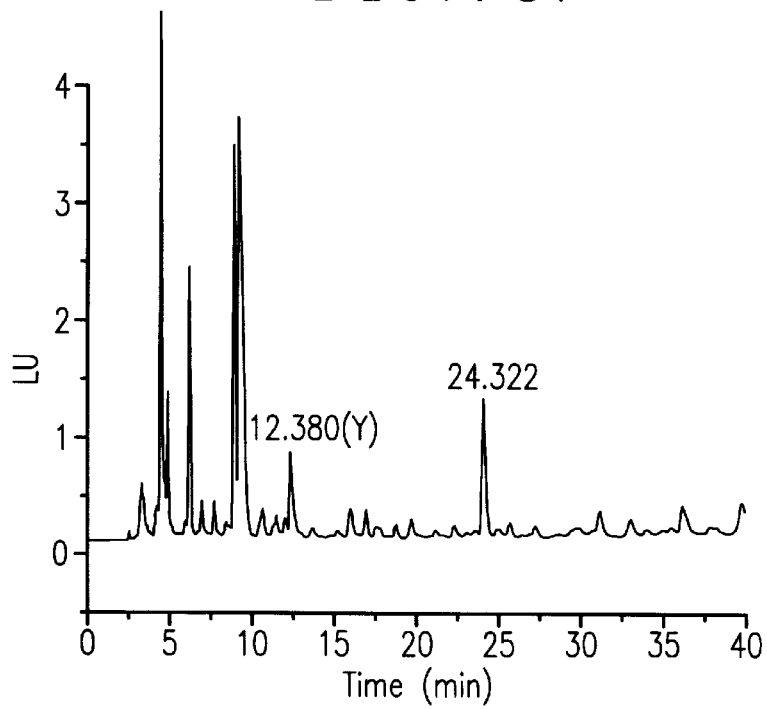
FIG. 16 is a graph illustrating the fluorescent compounds present in a flour sample.

Monitoring and/or measuring tyrosine bond formation may now be used to consistently produce optimum dough products. Standards for tyrosine bond content corresponding to different dough applications and different processing stages may now be found and used as a comparison or guide to direct dough processing. Moreover, the tyrosine content in flour may also be found and used to both predict dough characteristics and precalibrate dough processing equipment such that waste is minimized and optimum products are consistently produced. Knowledge of this starting tyrosine and/or tyrosine bond content allows for prediction of the potential for tyrosine bond formation since the tyrosine present in the flour is the tyrosine used to form tyrosine bonds. A sample of flour exhibiting high levels of tyrosine should have the potential to form a higher number of tyrosine bonds. This in turn may contribute to a higher rate of tyrosine bond formation and therefore, shorter mixing times for dough formation. Moreover, a high starting tyrosine content may also indicate the need for modification such as increasing the pH of the dough or the addition of metal chelating agents or free tyrosine to retard tyrosine bond formation. Conversely, a flour exhibiting a lower level of tyrosine may need longer mixing times to form a high quality dough and/or some modification to promote tyrosine bond formation (i.e. the addition of oxidizing agents or decreasing the pH of the dough). The tyrosine content of flour may be measured through derivatized or underivatized amino acids, however, measuring the derivatized amino acids is a much more sensitive technique. An example of determining the tyrosine content of flour using HPLC of the underivatized amino acids is shown in FIG. 16. Tyrosine is represented by the peak which elutes at 12.380 minutes.

Conclusion

Since tyrosine bond levels and the formation of tyrosine bonds were heretofore unrelated to dough formation capabilities and since the content of tyrosine and tyrosine bonds as well as tyrosine bond formation may be assessed both prior to and during dough production, dough production can be effected such that optimum dough products are consistently produced based on the knowledge of the tyrosine and/or tyrosine bond content of the starting flour, assessment of tyrosine bonding during dough production and modification of tyrosine bond formation during dough production in response to the assessment in order to achieve an ideal tyrosine bond content based on the eventual end use of the dough produced.

I claim:

1. A method of making a dough comprising the steps of:
    combining dough-forming ingredients to form a dough and mixing the dough;
    during said mixing step, periodically analyzing the dough to determine respective approximate ranges of the number of tyrosine bonds therein; and
    comparing said analyzed ranges of tyrosine bonds to a predetermined optimum range standard in order to achieve an optimum range of tyrosine bonds in the dough.

2. The method of claim 1 further including the step of manipulating the range of tyrosine bonds within said dough.

3. The method of claim 1 further including the step of stopping the mixing when the predetermined optimum range is reached.

4. The method of claim 1 wherein the periodic analyzing of the dough is done by fluorometry.

5. The method of claim 2 wherein said manipulation step is chosen from a group comprising adding an amount of oxidizing agent to the dough, adding an amount of metal chelating agent to the dough, adding an amount of free tyrosine or tyrosine analogues to the dough, adjusting the pH of the dough, altering the mixing time, and combinations thereof.

6. The method of claim 2 wherein the manipulation of the number of tyrosine bonds is accomplished by adding an oxidizing agent to the dough.

7. The method of claim 6 wherein said oxidizing agent is ascorbic acid.

8. The method of claim 6 wherein said oxidizing agent is potassium bromate.

9. The method of claim 2 wherein the manipulation of the number of tyrosine bonds is accomplished by adding free tyrosine and/or analogs thereof to the dough.

10. The method of claim 2 wherein the manipulation of the number of tyrosine bonds is accomplished by adding a metal chelating agent to the dough.

11. The method of claim 2 wherein the manipulation of the number of tyrosine bonds is accomplished by adjusting the pH of the dough.

12. The method of claim 2 wherein said manipulation of the number of tyrosine bonds in the dough is done in response to said comparison of said analyzed tyrosine range to said predetermined range.

13. The method of claim 12 wherein said manipulation of the number of tyrosine bonds in the dough is controlled by a computer program configured to achieve the desired range of tyrosine bonds by directing said manipulation in response to said analysis.

14. The method of claim 1 wherein said tyrosine bonds analyzed include tyrosine bonded with a moiety selected from a group comprising tyrosine, quinones, hydroquinone, dihydroxyphenylalanine (DOPA), dopaquinone, semiquinones, glutathione (GSH), cysteine, catechols, various carbohydrates and combinations thereof.

* * * * *